United States Patent
Yoganathan et al.

(10) Patent No.: US 6,830,925 B2
(45) Date of Patent: Dec. 14, 2004

(54) CAMK-X1 AND ITS USES

(75) Inventors: Thillainathan Yoganathan, Richmond (CA); Allen Delaney, Vancouver (CA)

(73) Assignee: QLT Inc., Vancouver (CA)

( * ) Notice: Subject to any disclaimer, the term of this patent is extended or adjusted under 35 U.S.C. 154(b) by 0 days.

(21) Appl. No.: 09/960,643

(22) Filed: Sep. 20, 2001

(65) Prior Publication Data

US 2002/0088013 A1 Jul. 4, 2002

Related U.S. Application Data

(60) Provisional application No. 60/233,999, filed on Sep. 20, 2000.

(51) Int. Cl.$^7$ .......................... C12N 15/63; C07H 21/04
(52) U.S. Cl. .................. 435/320.1; 536/23.1; 536/24.1; 536/23.5
(58) Field of Search .............................. 536/23.1, 23.5; 435/320.1

(56) References Cited

U.S. PATENT DOCUMENTS

2002/0197679 A1 * 12/2002 Tang et al.

FOREIGN PATENT DOCUMENTS

WO          WO 00/35946 A1      6/2000

OTHER PUBLICATIONS

Tang et al. Accession No. AAI60703, 2000.*
Rhodes et al. Accession No. AL049688, Apr. 21, 1999.*
Tang et al. Accession No. AAM41547, 2000.*
Rhodes et al. GenEmbl Accession No. AL049688, Apr. 21, 1999.*
Grafham et al. GenEmbl Accession No. ALO23754, Locus HS272L16, Nov. 23, 1999.*
Bowie et al., 1990. Science, vol. 247, pp. 1306–1310.*
Ngo et al, The Protein Folding Problem and Tertiary Structure Prediction, 1994, Merz er (ed.), pp. 433&492–495.*
Rudlinger J in Peptide Hormones. Editor Parsons JA. pp. 1–7, 1976 University Park Press, Baltimore.*
Heist, Kevin E. et al., The role of $Ca^2$ +/calmodulin–dependent protein kinases within the nucleus, Invited review, Cell Calcium, (1998), pp. 103–114, Harcourt Brace & Co. Ltd.
Hiroyuki, Minami et al., The Effect of KN–62, $Ca^2$ +/Calmodulin–Dependent Protein Kinase II Inhibitor on Cell Cycle, Biochemical and Biophysical Research Communications, Feb. 28, 1994, pp. 241–248, vol. 199, No. 1, 1994, Academic Press, Inc.
Schultz, Jorg et al., More than 1,000 putative new human signaling proteins revealed by EST data mining, Nature Genetics, Jun. 2000, pp. 201–204, vol. 25, Nature America Inc.
Soderling, Thomas R. et al., The $Ca^2$ +/calmodulin–dependent protein kinase cascade, Previews, Tibs 24, Jun. 1999.
Williams, Carol L. et al., Expression of $Ca^2$ +/Calmodulin–Dependent Protein Kinase Types II and IV, and Reduced DNA Synthesis Due to the $Ca^2$ +/Calmodulin–Dependent Protein Kinase Inhibitor KN–62 (1–[N, O–Bis(5–isoquinolinesulfonyl)–N–methyl–L–tyrosyl]–4–phenylpiperazine) in Small Cell Lung Carcinoma, Biochemical Pharmacology, 1996, pp. 707–715, vol. 51, Elsevier Science Inc.

* cited by examiner

Primary Examiner—Ram R. Shukla
(74) Attorney, Agent, or Firm—Pamela J. Sherwood; Bozicevic, Field & Francis LLP

(57) ABSTRACT

Methods for isolating CaMK-X1 genes are provided. The CaMK-X1 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

6 Claims, 2 Drawing Sheets

Kinase Activities of Expressed CaMKXI

A. CaMKXI Expressed in Hi5 Cell

B. CaMKXI Expressed in 293 Cell

SEQUENCE LISTING

<160> NUMBER OF SEQ ID NOS: 13

<210> SEQ ID NO 1
<211> LENGTH: 2447
<212> TYPE: DNA
<213> ORGANISM: H. sapiens
<220> FEATURE:
<221> NAME/KEY: CDS
<222> LOCATION: (70)...(1498)

<400> SEQUENCE: 1

```
tggagtggga gctcaagcag gattcttccc gagtccctgg catcctcaga agcttcaact        60 ctggaggca atg ggt cga aag gaa gaa gat gac tgc agt tcc tgg aag aaa       111
          Met Gly Arg Lys Glu Glu Asp Asp Cys Ser Ser Trp Lys Lys
            1               5                  10 cag acc acc aac atc cgg aaa acc ttc att ttt atg gaa gtg ctg gga       159
Gln Thr Thr Asn Ile Arg Lys Thr Phe Ile Phe Met Glu Val Leu Gly
 15                  20                  25                  30 tca gga gct ttc tca gaa gtt ttc ctg gtg aag caa aga ctg act ggg       207
Ser Gly Ala Phe Ser Glu Val Phe Leu Val Lys Gln Arg Leu Thr Gly
                 35                  40                  45 aag ctc ttt gct ctg aag tgc atc aag aag tca cct gcc ttc cgg gac       255
Lys Leu Phe Ala Leu Lys Cys Ile Lys Lys Ser Pro Ala Phe Arg Asp
     50                  55                  60 agc agc ctg gag aat gag att gct gtg ttg aaa aag atc aag cat gaa       303
Ser Ser Leu Glu Asn Glu Ile Ala Val Leu Lys Lys Ile Lys His Glu
 65                  70                  75 aac att gtg acc ctg gag gac atc tat gag agc acc acc cac tac tac       351
Asn Ile Val Thr Leu Glu Asp Ile Tyr Glu Ser Thr Thr His Tyr Tyr
                 80                  85                  90 ctg gtc atg cag ctt gtt tct ggt ggg gag ctc ttt gac cgg atc ctg       399
Leu Val Met Gln Leu Val Ser Gly Gly Glu Leu Phe Asp Arg Ile Leu
             95                 100                 105                 110 gag cgg ggt gtc tac aca gag aag gat gcc agt ctg gtg atc cag cag       447
Glu Arg Gly Val Tyr Thr Glu Lys Asp Ala Ser Leu Val Ile Gln Gln
                    115                 120                 125 gtc ttg tcg gca gtg aaa tac cta cat gag aat ggc atc gtc cac aga       495
Val Leu Ser Ala Val Lys Tyr Leu His Glu Asn Gly Ile Val His Arg
             130                 135                 140 gac tta aag ccc gaa aac ctg ctt tac ctt acc cct gaa gag aac tct       543
Asp Leu Lys Pro Glu Asn Leu Leu Tyr Leu Thr Pro Glu Glu Asn Ser
         145                 150                 155 aag atc atg atc act gac ttt ggt ctg tcc aag atg gaa cag aat ggc       591
Lys Ile Met Ile Thr Asp Phe Gly Leu Ser Lys Met Glu Gln Asn Gly
     160                 165                 170 atc atg tcc act gcc tgt ggg acc cca ggc tac gtg gct cca gaa gtg       639
Ile Met Ser Thr Ala Cys Gly Thr Pro Gly Tyr Val Ala Pro Glu Val
175                 180                 185                 190 ctg gcc cag aaa ccc tac agc aag gct gtg gat tgc tgg tcc atc ggc       687
Leu Ala Gln Lys Pro Tyr Ser Lys Ala Val Asp Cys Trp Ser Ile Gly
                 195                 200                 205 gtc atc acc tac ata ttg ctc tgt gga tac ccc ccg ttc tat gaa gaa       735
Val Ile Thr Tyr Ile Leu Leu Cys Gly Tyr Pro Pro Phe Tyr Glu Glu
             210                 215                 220 acg gag tct aag ctt ttc gag aag atc aag gag ggc tac tat gag ttt       783
Thr Glu Ser Lys Leu Phe Glu Lys Ile Lys Glu Gly Tyr Tyr Glu Phe
         225                 230                 235 gag tct cca ttc tgg gat gac att tct gag tca gcc aag gac ttt att       831
Glu Ser Pro Phe Trp Asp Asp Ile Ser Glu Ser Ala Lys Asp Phe Ile
```

-continued

```
              240                 245                 250
tgc cac ttg ctt gag aag gat ccg aac gag cgg tac acc tgt gag aag     879
Cys His Leu Leu Glu Lys Asp Pro Asn Glu Arg Tyr Thr Cys Glu Lys
255                 260                 265                 270 gcc ttg agt cat ccc tgg att gac gga aac acg gcc ctc cac cgg gac     927
Ala Leu Ser His Pro Trp Ile Asp Gly Asn Thr Ala Leu His Arg Asp
                275                 280                 285 atc tac cca tca gtc agc ctc cag atc cag aag aac ttt gct aag agc     975
Ile Tyr Pro Ser Val Ser Leu Gln Ile Gln Lys Asn Phe Ala Lys Ser
            290                 295                 300 aag tgg agg caa gcc ttc aac gca gca gct gtg gtg cac cac atg agg    1023
Lys Trp Arg Gln Ala Phe Asn Ala Ala Ala Val Val His His Met Arg
        305                 310                 315 aag cta cac atg aac ctg cac agc ccg ggc gtc cgc cca gag gtg gag    1071
Lys Leu His Met Asn Leu His Ser Pro Gly Val Arg Pro Glu Val Glu
    320                 325                 330 aac agg ccg cct gaa act caa gcc tca gaa acc tct aga ccc agc tcc    1119
Asn Arg Pro Pro Glu Thr Gln Ala Ser Glu Thr Ser Arg Pro Ser Ser
335                 340                 345                 350 cct gag atc acc atc acc gag gca cct gtc ctg gac cac agt gta gca    1167
Pro Glu Ile Thr Ile Thr Glu Ala Pro Val Leu Asp His Ser Val Ala
                355                 360                 365 ctc cct gcc ctg acc caa tta ccc tgc cag cat ggc cgc cgg ccc act    1215
Leu Pro Ala Leu Thr Gln Leu Pro Cys Gln His Gly Arg Arg Pro Thr
            370                 375                 380 gcc cct ggt ggc agg tcc ctc aac tgc ctg gtc aat ggc tcc ctc cac    1263
Ala Pro Gly Gly Arg Ser Leu Asn Cys Leu Val Asn Gly Ser Leu His
        385                 390                 395 atc agc agc agc ctg gtg ccc atg cat cag ggg tcc ctg gcc gcc ggg    1311
Ile Ser Ser Ser Leu Val Pro Met His Gln Gly Ser Leu Ala Ala Gly
    400                 405                 410 ccc tgt ggc tgc tgc tcc agc tgc ctg aac att ggg agc aaa gga aag    1359
Pro Cys Gly Cys Cys Ser Ser Cys Leu Asn Ile Gly Ser Lys Gly Lys
415                 420                 425                 430 tcc tcc tac tgc tct gag ccc aca ctc ctc aaa aag gcc aac aaa aaa    1407
Ser Ser Tyr Cys Ser Glu Pro Thr Leu Leu Lys Lys Ala Asn Lys Lys
                435                 440                 445 cag aac ttc aag tcg gag gtc atg gta cca gtt aaa gcc agt ggc agc    1455
Gln Asn Phe Lys Ser Glu Val Met Val Pro Val Lys Ala Ser Gly Ser
            450                 455                 460 tcc cac tgc cgg gca ggg cag act gga gtc tgt ctc att atg t          1498
Ser His Cys Arg Ala Gly Gln Thr Gly Val Cys Leu Ile Met
        465                 470                 475 gattcctgga gcctgtgcct atgtcactgc aattttcagg agacatattc aactcctctg  1558
ctcttccaaa cctggtgtct atccggcaga gggaggaagg cagagcaagt ggagcagggc  1618
ttagcaggag cagtttctgg ccagaagcac cagcctgctg ccagcggggc agcccctcat  1678
aggaggccca ggagggagcc ccaaggcgta gaagccttgt tgaagctgtg agcaggagaa  1738
gcggtgccca ccagcttcca ggtctccctg acctgcctgc tctatgcccc acaccctacg  1798
tgccgtggct ctgtgcagtg tacgtagata gctctcgcct gggtctgtgc tgtttgtcgt  1858
gaaaagctta atgggctggc aggctgtgt caccttctcc aagcaaagcc atatggagca  1918
tctacccaga ctcccactct gcacacactc actcccacct ctcaagcctc caacctcttg  1978
gccagattgg gctcattaat gtcgttgcct gcccatctgc atgaatgaca ggcagctccc  2038
catggtggtc tgcctgtgag ctcttcaagt tctaatcctt aactccagga ttagctccca  2098
agtgcgctga gacccagcca gcacacttct ggcccttctc cctgcctcaa tctaaaagca  2158
```

```
gtgccacacc ctccaaagtg gaatagaaag aagttcatga gtaagggctg caaggaattc    2218
ttatcctggc cacatgtcct ccgtgcacac acccaatgga gttaaccttg gaagttgact    2278
attttaatgt ctgccaggag ttctaatcct gcctctgttc ccttttctct ccttgaaagt    2338
ccagcacacc attcttgtcc ttccccagtt tcctcgccct ccaccccctcc agcttcatgc   2398 tcagtgttgt gcttaataaa atggacatat ttttctctaa aaaaaaaaa                2447
```

```
<210> SEQ ID NO 2
<211> LENGTH: 476
<212> TYPE: PRT
<213> ORGANISM: H. sapiens

<400> SEQUENCE: 2

Met Gly Arg Lys Glu Glu Asp Asp Cys Ser Ser Trp Lys Lys Gln Thr
  1               5                  10                  15

Thr Asn Ile Arg Lys Thr Phe Ile Phe Met Glu Val Leu Gly Ser Gly
             20                  25                  30

Ala Phe Ser Glu Val Phe Leu Val Lys Gln Arg Leu Thr Gly Lys Leu
         35                  40                  45

Phe Ala Leu Lys Cys Ile Lys Lys Ser Pro Ala Phe Arg Asp Ser Ser
     50                  55                  60

Leu Glu Asn Glu Ile Ala Val Leu Lys Lys Ile Lys His Glu Asn Ile
 65                  70                  75                  80

Val Thr Leu Glu Asp Ile Tyr Glu Ser Thr Thr His Tyr Tyr Leu Val
                 85                  90                  95

Met Gln Leu Val Ser Gly Gly Glu Leu Phe Asp Arg Ile Leu Glu Arg
            100                 105                 110

Gly Val Tyr Thr Glu Lys Asp Ala Ser Leu Val Ile Gln Gln Val Leu
        115                 120                 125

Ser Ala Val Lys Tyr Leu His Glu Asn Gly Ile Val His Arg Asp Leu
    130                 135                 140

Lys Pro Glu Asn Leu Leu Tyr Leu Thr Pro Glu Glu Asn Ser Lys Ile
145                 150                 155                 160

Met Ile Thr Asp Phe Gly Leu Ser Lys Met Glu Gln Asn Gly Ile Met
                165                 170                 175

Ser Thr Ala Cys Gly Thr Pro Gly Tyr Val Ala Pro Glu Val Leu Ala
            180                 185                 190

Gln Lys Pro Tyr Ser Lys Ala Val Asp Cys Trp Ser Ile Gly Val Ile
        195                 200                 205

Thr Tyr Ile Leu Leu Cys Gly Tyr Pro Pro Phe Tyr Glu Glu Thr Glu
    210                 215                 220

Ser Lys Leu Phe Glu Lys Ile Lys Glu Gly Tyr Tyr Glu Phe Glu Ser
225                 230                 235                 240

Pro Phe Trp Asp Asp Ile Ser Glu Ser Ala Lys Asp Phe Ile Cys His
                245                 250                 255

Leu Leu Glu Lys Asp Pro Asn Glu Arg Tyr Thr Cys Glu Lys Ala Leu
            260                 265                 270

Ser His Pro Trp Ile Asp Gly Asn Thr Ala Leu His Arg Asp Ile Tyr
        275                 280                 285

Pro Ser Val Ser Leu Gln Ile Gln Lys Asn Phe Ala Lys Ser Lys Trp
    290                 295                 300

Arg Gln Ala Phe Asn Ala Ala Val Val His His Met Arg Lys Leu
305                 310                 315                 320
```

-continued

```
His Met Asn Leu His Ser Pro Gly Val Arg Pro Glu Val Glu Asn Arg
            325                 330                 335

Pro Pro Glu Thr Gln Ala Ser Glu Thr Ser Arg Pro Ser Ser Pro Glu
            340                 345                 350

Ile Thr Ile Thr Glu Ala Pro Val Leu Asp His Ser Val Ala Leu Pro
            355                 360                 365

Ala Leu Thr Gln Leu Pro Cys Gln His Gly Arg Arg Pro Thr Ala Pro
370             375                 380

Gly Gly Arg Ser Leu Asn Cys Leu Val Asn Gly Ser Leu His Ile Ser
385             390                 395                 400

Ser Ser Leu Val Pro Met His Gln Gly Ser Leu Ala Ala Gly Pro Cys
            405                 410                 415

Gly Cys Cys Ser Ser Cys Leu Asn Ile Gly Ser Lys Gly Lys Ser Ser
            420                 425                 430

Tyr Cys Ser Glu Pro Thr Leu Leu Lys Lys Ala Asn Lys Lys Gln Asn
            435                 440                 445

Phe Lys Ser Glu Val Met Val Pro Val Lys Ala Ser Gly Ser Ser His
            450                 455                 460

Cys Arg Ala Gly Gln Thr Gly Val Cys Leu Ile Met
465                 470                 475

<210> SEQ ID NO 3
<211> LENGTH: 25
<212> TYPE: DNA
<213> ORGANISM: H. sapiens

<400> SEQUENCE: 3
gtggagggcg aggaaactgg ggaag                                               25

<210> SEQ ID NO 4
<211> LENGTH: 23
<212> TYPE: DNA
<213> ORGANISM: Homo sapiens

<400> SEQUENCE: 4
ggagggcgag gaaactgggg aag                                                 23

<210> SEQ ID NO 5
<211> LENGTH: 25
<212> TYPE: DNA
<213> ORGANISM: Homo sapiens

<400> SEQUENCE: 5
gtggagggcg aggaaactgg ggaag                                               25

<210> SEQ ID NO 6
<211> LENGTH: 31
<212> TYPE: DNA
<213> ORGANISM: Homo sapiens

<400> SEQUENCE: 6
ctcgagtcac ataatgagac agactccagt c                                        31

<210> SEQ ID NO 7
<211> LENGTH: 13
<212> TYPE: PRT
<213> ORGANISM: Homo sapiens

<400> SEQUENCE: 7

Lys Arg Arg Glu Ile Leu Ser Arg Arg Pro Ser Tyr Arg
```

```
<210> SEQ ID NO 8
<211> LENGTH: 15
<212> TYPE: PRT
<213> ORGANISM: Homo sapiens

<400> SEQUENCE: 8

Pro Leu Ala Arg Thr Leu Ser Val Ala Gly Leu Pro Gly Lys Lys
 1               5                  10                  15

<210> SEQ ID NO 9
<211> LENGTH: 10
<212> TYPE: PRT
<213> ORGANISM: Homo sapiens

<400> SEQUENCE: 9

Pro Leu Ser Arg Thr Leu Ser Val Ser Ser
 1               5                  10

<210> SEQ ID NO 10
<211> LENGTH: 30
<212> TYPE: DNA
<213> ORGANISM: Homo sapiens

<400> SEQUENCE: 10
gaattcaatg ggtcgaaagg aagaagatga                                    30

<210> SEQ ID NO 11
<211> LENGTH: 31
<212> TYPE: DNA
<213> ORGANISM: Homo sapiens

<400> SEQUENCE: 11
ctcgagtcac ataatgagac agactccagt c                                  31

<210> SEQ ID NO 12
<211> LENGTH: 30
<212> TYPE: DNA
<213> ORGANISM: Homo sapiens

<400> SEQUENCE: 12
gaattcaatg ggtcgaaagg aagaagatga                                    30

<210> SEQ ID NO 13
<211> LENGTH: 30
<212> TYPE: DNA
<213> ORGANISM: Homo sapiens

<400> SEQUENCE: 13
ctcgagctgg atctggaggc tgactgatgg                                    30
```

CAMK-X1 AND ITS USES

This application claims the benefit of U.S. Provisional Application No. 60/233,999, filed Sep. 20, 2000.

An accumulation of genetic changes underlies the development and progression of cancer, resulting in cells that differ from normal cells in their behavior, biochemistry, genetics, and microscopic appearance. Mutations in DNA that cause changes in the expression level of key proteins, or in the biological activity of proteins, are thought to be at the heart of cancer. For example, cancer can be triggered in part when genes that play a critical role in the regulation of cell division undergo mutations that lead to their overexpression.

Oncogenes are involved in the dysregulation of growth that occurs in cancers. An example of oncogene activity involves protein kinases, enzymes that help regulate many cellular activities, particularly signaling from the cell membrane to the nucleus, thus initiating the cell's entrance into the cell cycle and controlling several other functions.

Oncogenes may be tumor susceptibility genes, which are typically up-regulated in tumor cells, or may be tumor suppressor genes, which are down-regulated or absent in tumor cells. Malignancies can arise when a tumor suppressor is lost and/or an oncogene is inappropriately activated. When such mutations occur in somatic cells, they result in the growth of sporadic tumors.

Hundreds of genes have been implicated in cancer, but in most cases relationships between these genes and their effects are poorly understood. Using massively parallel gene expression analysis, scientists can now begin to connect these genes into related pathways.

Phosphorylation is important in signal transduction mediated by receptors for extracellular biological signals such as growth factors or hormones. For example, many cancer causing genes (oncogenes) are protein kinases, enzymes that catalyze protein phosphorylation reactions, or are specifically regulated by phosphorylation. In addition, a kinase can have its activity regulated by one or more distinct protein kinases, resulting in specific signaling cascades.

Many of the intracellular physiological activities in mammalian cells that involve $Ca^{++}$ as a second messenger are mediated by calmodulin (CAM). This ubiquitous $Ca^{++}$-binding protein has an ability to activate a variety of enzymes in a $Ca^{++}$-dependent manner. Among these enzymes are $Ca^{++}$ and calmodulin-dependent cyclic-nucleotide phosphodiesterase (CaM-PDE) and the calmodulin-dependent kinases.

CaM-kinases are involved in regulation of smooth muscle contraction (MLC kinase), glycogen breakdown (phosphorylase kinase), and neurotransmission (CaM-kinase I and CaM-kinase II). CaM-kinase I phosphorylates a variety of substrates including the neurotransmitter related proteins synapsin I and II, the gene transcription regulator, CREB, and the cystic fibrosis conductance regulator protein, CFTR (Haribabu et al. (1995) *EMBO Journal* 14:3679–86). CaM-kinase II also phosphorylates synapsin at different sites, and controls the synthesis of catecholamines in the brain through phosphorylation and activation of tyrosine hydroxylase.

Many of the CaM-kinases are activated by phosphorylation in addition to binding to CaM. The kinase may autophosphorylate, or be phosphorylated by another kinase as part of a "kinase cascade". A variety of substances inhibit the activation properties of calmodulin on the calmodulin-dependent enzymes. It has been shown that drugs that inhibit calmodulin sensitive processes are also potent inhibitors of the growth and viability of tumor cells (Hait et al. (1985) *Biochem Pharmacol.* 34:3973–3978; Hait et al. (1986) *J. Clin. Oncol.* 4:994–1012). Thus, substances that inhibit calmodulin-mediated enzyme activites may affect cell viability, and possibly other cellular phenomena, through their interactions with calmodulin.

Members of the CaM-kinase cascade in the cytosol regulate cell survival through activation of protein kinase B, and transcription through indirect activation of MAP kinases. Activated MAP kinases translocate to the nucleus, where they phosphorylate transcription factors. CaM-kinase IV can also phosphorylate and inactivate type I adenylate cyclase, thereby decreasing cyclic AMP levels.

Each member of the CaM-kinase cascade has a catalytic domain adjacent to a regulatory region that contains an overlapping auto-inhibitory domain (AID) and the CaM-binding domain (CBD). An interaction between the AID and the catalytic domain maintains the kinase in an inactive conformation by preventing binding of protein substrate as well as $Mg^{++}$-ATP. Binding of $Ca^{++}$-CaM to the CBD alters the conformation of the overlapping AID such that it no longer interferes with substrate binding; the kinase is therefore active. As in the cases of other protein kinases, CaMKI has a catalytic cleft between its upper and lower lobes, which are responsible for binding $Mg^{++}$-ATP and protein substrates, respectively. At the base of their catalytic clefts, many protein kinases, including CaMKI and CaMKIV, have an activation loop containing a threonine residue whose phosphorylation strongly augments kinase activity.

Cloning procedures aided by homology searches of EST databases have accelerated the pace of discovery of new genes, but EST database searching remains an involved and onerous task. More than 1.6 million human EST sequences have been deposited in public databases, making it difficult to identify ESTs that represent new genes. Compounding the problems of scale are difficulties in detection associated with a high sequencing error rate and low sequence similarity between distant homologues.

Relevant Literature

The use of genomic sequence in data mining for signaling proteins is discussed in Schultz et al. (2000) *Nature Genetics* 25:201.

The CaM-kinase protein family has been reviewed, for example by Heist et al. (1998) *Cell Calcium* 23(2–3): 103–14; and Soderling (1999) *Trends Biochem Sci* 24(6): 232–6. Inhibitors of calmodulin mediated enzymes are described in U.S. Pat. No. 5,386,019. The effects of CaM-kinase inhibitors include inhibition of DNA synthesis and slowed progression through S phase, discussed by Minami et al. (1994) *Biochem Biophys Res. Comm.* 199:241–248; and Williams et al. (1996) *Biochem Pharmacol.* 51:707–715.

The gene accession number for EST clone K283 is AA838372.

SUMMARY OF THE INVENTION

This invention relates to novel CaMK-X1 nucleic acid compositions and their encoded polypeptides and variants thereof, to genes corresponding to these nucleic acids and to proteins expressed by the genes. The invention also provides diagnostics and therapeutics comprising such novel human nucleic acids, their corresponding genes or gene products, including probes, antisense nucleotides, and antibodies. The nucleic acids of the invention encode a protein designated as CaMK-X1. CaMK-X1 is associated with cellular transformation and regulation. The upregulated expression of this gene in cancer tissues provides a genetic target to screen therapeutics for the treatment of cancer and various other diseases. In addition, the sequence is used to form antisense compositions for the control of disease, to perform research using transgenic or knockout animal models, and research reagents such as antibodies, cell assays, and chromatographic reagents.

The nucleic acid compositions find use in identifying homologous or related genes; for production of the encoded protein; in producing compositions that modulate the expression or function of its encoded protein; for gene therapy; in mapping functional regions of the protein; and in studying associated physiological pathways. In addition, modulation of the gene activity in vivo is used for prophylactic and therapeutic purposes, such as treatment of cancer, identification of cell type based on expression, and the like.

DESCRIPTION OF THE SPECIFIC EMBODIMENTS

Figure 1:
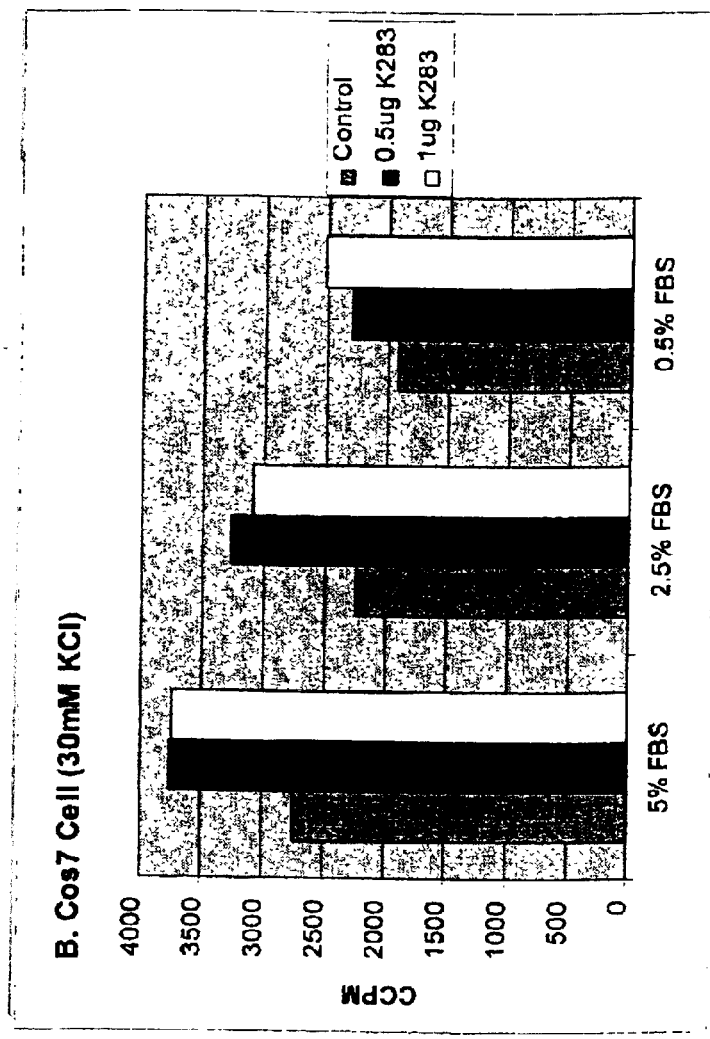
FIG. 1 is a graph depicting the proliferation of Cos 7 cells that were transfected with increasing concentrations of CaMK-X1 or vector plasmids in the presence of KCl.

The invention provides novel nucleic acids encoding a polypeptide identified herein as CaMK-X1, which is a member of the calmodulin dependent kinase (CaM-kinase) family. Specifically, CaMK-X1 is found to be upregulated in cancer tissues. Thus, this newly discovered gene is associated with cellular transformation and regulation.

The nucleic acid compositions of the subject invention find use in identifying homologous or related genes; for production of the encoded protein; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes, such as treatment of cancer, identification of cell type based on expression, and the like. The protein is useful as an immunogen for producing specific antibodies, in screening for biologically active agents that act in the integrin signaling pathway and for therapeutic and prophylactic purposes.

Products that modulate the expression and/or activity of CaMK-X1 have a therapeutic effect in the treatment of cancer, leukemia, solid tumors, chronic or acute inflammatory disease, restenosis, diabetes, neurological disorders, arthritis and osteoporosis, among other indications.

Characterization of CaMK-X1

The human gene sequence encoding CaMK-X1, which maps to chromosome 1q32.1–32.3, is provided as SEQ ID NO:1, and the encoded polypeptide product is provided as SEQ ID NO:2. The open reading frame of the sequence is indicated in the seqlist of SEQ ID NO:1, and starts at position 70. The sequence of this mRNA was used to deduce the 542 primary amino acid sequence of the protein. Dot blot analysis of probes prepared from mRNA of tumors showed that expression of CaMK-X1 is consistently up-regulated in human tumor tissue.

The invention includes, but is not necessarily limited to, nucleic acids having a sequence set forth in SEQ ID NO:1; nucleic acids that hybridize under stringent conditions, particularly conditions of high stringency, to the sequence set forth in SEQ ID NO:1; genes corresponding to the provided nucleic acids; partial sequences encoding functional domain of CaMK-X1; and fragments and derivatives thereof. Other nucleic acid compositions contemplated by and within the scope of the present invention will be readily apparent to one of ordinary skill in the art when provided with the disclosure herein.

The nucleic acids of the invention include nucleic acids having sequence similarity or sequence identity to SEQ ID NO:1. Nucleic acids having sequence similarity are detected by hybridization under low stringency conditions, for example, at 50° C. and 10× SSC (0.9 M saline/0.09 M sodium citrate) and remain bound when subjected to washing at 55° C. in 1× SSC. Sequence identity can be determined by hybridization under stringent conditions, for example, at 50° C. or higher and 0.1× SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to SEQ ID NO:1 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, yeast, nematodes, etc.

In one embodiment, hybridization is performed using at least 18 contiguous nucleotides (nt) of at least one of SEQ ID NO:1. That is, when at least 18 contiguous nt of SEQ ID NO. 1 are used as a probe, the probe will preferentially hybridize with a nucleic acid comprising the complementary sequence, allowing the identification and retrieval of the nucleic acids that uniquely hybridize to the selected probe. Probes of more than 18 nt can be used, e.g., probes of from about 18 nt to about 25, 50, 100, 250, or 500 nt, but 18 nt represents sufficient sequence for unique identification.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25–30% base pair (bp) mismatches relative to the selected nucleic acid probe. In general, allelic variants contain 15–25% bp mismatches, and can contain as little as 5–15%, or 2–5%, or 1–2% bp mismatches, as well as a single bp mismatch.

The invention also encompasses homologs corresponding to the nucleic acids of SEQ ID NO:1, where the source of homologous genes can be any mammalian species, e.g., primate species, particularly human; rodents, such as rats; canines, felines, bovines, ovines, equines, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul, et al.

*Nucleic Acids Res.* (1997) 25:3389–3402. In general, variants of the invention have a sequence identity greater than at least about 65%, preferably at least about 75%, more preferably at least about 85%, and can be greater than at least about 90% or more.

The subject nucleic acids can be cDNAs or genomic DNAs, as well as fragments thereof, particularly fragments that encode a biologically active polypeptide and/or are useful in the methods disclosed herein (e.g., in diagnosis, as a unique identifier of a differentially expressed gene of interest, etc.) The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA can be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, about 500 to about 1500 contiguous nt selected from the nucleic acid sequence as shown in SEQ ID NO:1. For the most part, fragments will be of at least 18 nt, usually at least 25 nt, and up to at least about 50 contiguous nt in length or more. In one preferred embodiment, the nucleic acid molecules comprise a contiguous sequence of at least 18 nt selected from the group consisting of the nucleic acids shown in SEQ ID NO: 1.

Probes specific to the nucleic acid of the invention can be generated using the nucleic acid sequence disclosed in SEQ ID NO:1. The probes are preferably at least about 18 nt, 25 nt or more of the corresponding contiguous sequence of SEQ ID NO:1, and are usually less than about 2, 1, or 0.5 kb in length. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of a nucleic acid of one of SEQ ID NO:1. More preferably, probes are designed based on a contiguous sequence of one of the subject nucleic acids that remain unmasked following application of a masking program for masking low complexity (e.g., BLASTX) to the sequence., i.e., one would select an unmasked region, as indicated by the nucleic acids outside the poly-n stretches of the masked sequence produced by the masking program.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Polypeptide Compositions

The present invention further provides polypeptides encoded by SEQ ID NO. 1 and variants thereof, which can be used for a variety of purposes. The polypeptides contemplated by the invention include those encoded by the disclosed nucleic acids, as well as nucleic acids that, by virtue of the degeneracy of the genetic code, are not identical in sequence to the disclosed nucleic acids, and vairants thereof.

In general, the term "polypeptide" as used herein refers to both the full length polypeptide encoded by the recited nucleic acid, the polypeptide encoded by the gene represented by the recited nucleic acid, as well as portions or fragments thereof. "Polypeptides" also includes variants of the naturally occurring proteins, where such variants are homologous or substantially similar to the naturally occurring protein, and can be of an origin of the same or different species as the naturally occurring protein (e.g., human, murine, or some other species that naturally expresses the recited polypeptide, usually a mammalian species). In general, variant polypeptides have a sequence that has at least about 80%, usually at least about 90%, and more usually at least about 98% sequence identity with a differentially expressed polypeptide described herein, as measured by BLAST 2.0 using the parameters described above. The variant polypeptides can be naturally or non-naturally glycosylated, i.e., the polypeptide has a glycosylation pattern that differs from the glycosylation pattern found in the corresponding naturally occurring protein.

In general, the polypeptides of the subject invention are provided in a non-naturally occurring environment, e.g. are separated from their naturally occurring environment. In certain embodiments, the subject protein is present in a composition that is enriched for the protein as compared to a control. As such, purified polypeptides are provided, where by purified is meant that the protein is present in a composition that is substantially free of non-differentially expressed polypeptides, where by substantially free is meant that less than 90%, usually less than 60% and more usually less than 50% of the composition is made up of non CaMK-X1 polypeptides.

Variant polypeptides can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the protein (e.g., a functional domain and/or, where the polypeptide is a member of a protein family, a region associated with a consensus sequence).

Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a polypeptide encoded by SEQ ID NO:1, or a homolog thereof. Polypeptide regions of interest include the catalytic cleft, including activation loop, the auto-inhibitory domain, and the CaM-binding domain.

Antibodies Specific For CaMK-X1 Polypeptides

The present invention provides antibodies, which may be isolated antibodies, specific for CaMK-X1 polypeptides, e.g. any one of the variants, polypeptides, or domains described above. Such antibodies are useful, for example, in methods of detecting the presence of CaMK-X1 in a biological sample, and in methods of isolating CaMK-X1 from a biological sample.

The CaMK-X1 polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a CaMK-X1 polypeptide, particularly a human CaMK-X1 polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Diagnostic Uses

DNA-based reagents derived from the sequence of CaMK-X1, e.g. PCR primers, oligonucleotide or cDNA probes having a sequence set forth in SEQ ID NO:1, as well as antibodies against CaMK-X1, are used to screen patient samples, e.g. biopsy-derived tumors, inflammatory samples such as arthritic synovium, etc., for amplified CaMK-X1 DNA, or increased expression of CaMK-X1 mRNA or protein. DNA-based reagents are also designed for evaluation of chromosomal loci implicated in certain diseases e.g. for use in loss-of-heterozygosity (LOH) studies, or design of primers based on CaMK-X1 coding sequence.

The polynucleotides of the invention can be used to detect differences in expression levels between two cells, e.g., as a method to identify abnormal or diseased tissue in a human. The tissue suspected of being abnormal or diseased can be derived from a different tissue type of the human, but preferably it is derived from the same tissue type; for example, an intestinal polyp or other abnormal growth should be compared with normal intestinal tissue. The normal tissue can be the same tissue as that of the test sample, or any normal tissue of the patient, especially those that express the polynucleotide-related gene of interest (e.g., brain, thymus, testis, heart, prostate, placenta, spleen, small intestine, skeletal muscle, pancreas, and the mucosal lining of the colon, etc.). A difference between the polynucleotide-related gene, mRNA, or protein in the two tissues which are compared, for example, in molecular weight, amino acid or nucleotide sequence, or relative abundance, indicates a change in the gene, or a gene which regulates it, in the tissue of the human that was suspected of being diseased.

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a CaMK-X1 coding region or control regions is associated with disease, particularly cancers and other growth abnormalities. Diseases of interest may also include restenosis, diabetes, neurological disorders, etc. Disease associated polymorphisms may include deletion or truncation of the gene, mutations that alter expression level, that affect the binding activity of the protein, the kinase activity domain, etc.

Changes in the promoter or enhancer sequence that may affect expression levels of CaMK-X1 can be compared to expression levels of the normal allele by various methods known in the art. Methods for determining promoter or enhancer strength include quantitation of the expressed natural protein; insertion of the variant control element into a vector with a reporter gene such as beta-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express CaMK-X1 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp.14.2–14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type CaMK-X1 sequence. Hybridization with the variant sequence may also be used to determine its presence, by Southern blots, dot blots, etc. The hybridization pattern of a control and variant sequence to an array of oligonucleotide probes immobilised on an array, may also be used as a means of detecting the presence of variant sequences. Single strand conformational polymorphism (SSCP) analysis, denaturing gradient gel electrophoresis(DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in CaMK-X1 may be based on the functional or antigenic characteristics of the protein. Protein truncation assays are useful in detecting deletions that may affect the biological activity of the protein. Various immunoassays designed to detect polymorphisms in CaMK-X1 proteins may be used in screening. Where many diverse genetic mutations lead to a particular disease phenotype, functional protein assays have proven to be effective screening tools. The activity of the encoded CaMK-X1 protein in kinase assays, etc., may be determined by comparison with the wild-type protein.

Antibodies specific for CaMK-X1 may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal CaMK-X1 in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent, where final detection uses a substrate that undergoes a color change in the presence of the peroxidase. Alternatively, the secondary antibody may be conjugated to a flourescent compound, e.g. flourescein rhodamine, Texas red, etc. The absence or presence of antibody binding may be determined by various methods, including flow cytometry of dissociated cells, microscopy, radiography, scintillation counting, etc.

In some embodiments, the methods are adapted for use in vivo, e.g., to locate or identify sites where cancer cells are present. In these embodiments, a detectably-labeled moiety, e.g., an antibody, which is specific for CaMK-X1 is administered to an individual (e.g., by injection), and labeled cells are located using standard imaging techniques, including, but not limited to, magnetic resonance imaging, computed tomography scanning, and the like. In this manner, cancer cells are differentially labeled.

Diagnostic screening may also be performed for polymorphisms that are genetically linked to a predisposing mutation, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) *Genomics* 24:225–233; Ziegle et al. (1992) *Genomics* 14:1026–1031; Dib et al., supra.

The detection methods can be provided as part of a kit. Thus, the invention further provides kits for detecting the presence of an mRNA encoding CaMK-X1, and/or a polypeptide encoded thereby, in a biological sample. Procedures using these kits can be performed by clinical laboratories, experimental laboratories, medical practitioners, or private individuals. The kits of the invention for detecting a polypeptide comprise a moiety that specifically binds the polypeptide, which may be a specific antibody. The kits of the invention for detecting a nucleic acid comprise a moiety that specifically hybridizes to such a nucleic acid. The kit may optionally provide additional components that are useful in the procedure, including, but not limited to, buffers, developing reagents, labels, reacting surfaces, means for detection, control samples, standards, instructions, and interpretive information.

Genetically Altered Cell or Animal Models For CaMK-X1 Function

The subject nucleic acids can be used to generate transgenic animals or site specific gene modifications in cell lines. Transgenic animals may be made through homologous recombination, where the normal CaMK-X1 locus is altered. Alternatively, a nucleic acid construct is randomly integrated into the genome. Vectors for stable integration include plasmids, retroviruses and other animal viruses, YACs, and the like.

The modified cells or animals are useful in the study of CaMK-X1 function and regulation. For example, a series of small deletions and/or substitutions may be made in the CaMK-X1 gene to determine the role of different exons in kinase activity, oncogenesis, signal transduction, etc. Of interest are the use of CaMK-X1 to construct transgenic animal models for cancer, where expression of CaMK-X1 is specifically reduced or absent. Specific constructs of interest include antisense CaMK-X1, which will block CaMK-X1 expression and expression of dominant negative CaMK-X1 mutations. A detectable marker, such as lac Z may be introduced into the CaMK-X1 locus, where up-regulation of CaMK-X1 expression will result in an easily detected change in phenotype.

One may also provide for expression of the CaMK-X1 gene or variants thereof in cells or tissues where it is not normally expressed or at abnormal times of development. By providing expression of CaMK-X1 protein in cells in which it is not normally produced, one can induce changes in cell behavior, e.g. in the control of cell growth and tumorigenesis.

DNA constructs for homologous recombination will comprise at least a portion of the CaMK-X1 gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection, e.g. markers conferring resistance or susceptibility to antibiotics, are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals, domestic animals, etc. The transgenic animals may be used in functional studies, drug screening, etc., e.g. to determine the effect of a candidate drug on oncogenesis, etc.

Nucleic Acids Arrays

Arrays provide a high throughput technique that can assay a large number of polynucleotides or polypeptides in a sample. This technology can be used as a tool to test for differential expression. A variety of methods of producing arrays, as well as variations of these methods, are known in the art and contemplated for use in the invention. For example, arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions. Samples of nucleic acids can be detectably labeled (e.g., using radioactive or fluorescent labels) and then hybridized to the probes. Double stranded nucleic acids, comprising the labeled sample polynucleotides bound to probe nucleic acids, can be detected once the unbound portion of the sample is washed away. Alternatively, the nucleic acids of the test sample can be immobilized on the array, and the probes detectably labeled.

Techniques for constructing arrays and methods of using these arrays are described in, for example, Schena et al. (1996) *Proc Natl Acad Sci U S A.* 93(20):10614–9; Schena et al. (1995) *Science* 270(5235):467–70; Shalon et al. (1996) *Genome Res.* 6(7):639–45 U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

Arrays can be used to, for example, examine differential expression of genes and can be used to determine gene function. For example, arrays can be used to detect differential expression of CaMK-X1, where expression is compared between a test cell and control cell (e.g., cancer cells and normal cells). High expression of a particular message in a cancer cell, which is not observed in a corresponding normal cell, indicates a cancer specific gene product. Exemplary uses of arrays are further described in, for example, Pappalarado et al., *Sem. Radiation Oncol.* (1998) 8:217; and Ramsay, *Nature Biotechnol.* (1998) 16:40. Furthermore, many variations on methods of detection using arrays are well within the skill in the art and within the scope of the present invention. For example, rather than immobilizing the probe to a solid support, the test sample can be immobilized on a solid support which is then contacted with the probe.

Modulation of CaMK-X1 Expression

The CaMK-X1 genes, gene fragments, or the encoded protein or protein fragments are useful in therapy to treat disorders associated with CaMK-X1 defects. From a therapeutic point of view, inhibiting CaMK-X1 activity has a therapeutic effect on a number of proliferative disorders, including inflammation, restenosis, and cancer. Inhibition is achieved in a number of ways. Antisense CaMK-X1 sequences may be administered to inhibit expression. Pseudo-substrate inhibitors, for example, a peptide that mimics a substrate for CaMK-X1 may be used to inhibit activity. Other inhibitors are identified by screening for biological activity in an CaMK-X1 based functional assay, e.g. in vitro or in vivo CaMK-X1 kinase activity.

Expression vectors may be used to introduce the CaMK-X1 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or CaMK-X1 protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold micro projectiles are coated with the CaMK-X1 or DNA, then bombarded into skin cells.

Antisense molecules can be used to down-regulate expression of CaMK-X1 in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'—OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to antisense inhibitors, catalytic nucleic acid compounds, e.g. ribozymes, antisense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 95/23225, and Beigelman et al. (1995) *Nucl. Acids Res* 23:4434–42). Examples of oligonucleotides with catalytic activity are described in WO 95/06764. Conjugates of antisense ODN with a metal complex, e.g. terpyridyl Cu(II), capable of mediating mRNA hydrolysis are described in Bashkin et al. (1995) *Appl Biochem Biotechnol* 54:43–56.

Modulation of CaMK-X1 Activity

Agents that block CaMK-X1 activity provide a point of intervention in an important signaling pathway. Numerous agents are useful in reducing CaMK-X1 activity, including agents that directly modulate CaMK-X1 expression as described above, e.g. expression vectors, antisense specific for CaMK-X1; and agents that act on the CaMK-X1 protein, e.g. CaMK-X1 specific antibodies and analogs thereof, small organic molecules that block CaMK-X1 catalytic activity, etc.

The phosphorylation of proteins plays a key role in the transduction of extracellular signals into the cell. The enzymes that effect such phosphorylations are targets for the action of growth factors, hormones, and other agents involved in cellular metabolism, proliferation and differentiation.

In one embodiment of the invention, the activity of CaMK-X1 is modulated through calmodulin. For example, calmodulin inhibitors are known in the art, see U.S. Pat. No. 5,840,697, Blondelle; and U.S. Pat. No. 5,698,518, Carson et al.

Compound Screening

The availability of a number of components in the signaling pathways allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other etc. For example, one or more members of the CaM-kinase family may be combined with calmodulin in the absence or presence of calcium, and/or in the presence of CaM-kinase kinase. The components may be modified by sequence deletion, substitution, etc. to determine the functional role of specific domains.

Drug screening may be performed using an in vitro model, a genetically altered cell or animal, or purified CaMK-X1 protein. One can identify ligands or substrates that bind to, modulate or mimic the action of CaMK-X1. Areas of investigation include the development of treatments for hyper-proliferative disorders, e.g. cancer, restenosis, osteoarthritis, metastasis, etc.

Drug screening identifies agents that modulate CaMK-X1 function. Agents that mimic its function are predicted to activate the process of cell division and growth. Conversely, agents that inhibit CaMK-X1 function may inhibit transformation. Of particular interest are screening assays for agents that have a low toxicity for human cells. A wide variety of assays may be used for this purpose, including labeled in vitro protein—protein binding assays, electrophoretic mobility shift assays, immunoassays for protein binding, and the like. Knowledge of the 3-dimensional structure of CaMK-X1, derived from crystallization of purified recombinant CaMK-X1 protein, could lead to the rational design of small drugs that specifically inhibit CaMK-X1 activity. These drugs may be directed at specific domains of CaMK-X1, e.g. the kinase catalytic domain, the regulatory domain, the auto-inhibitory domain, etc.

The term "agent" as used herein describes any molecule, e.g. protein or pharmaceutical, with the capability of altering or mimicking the physiological function of CaMK-X1. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic CaMK-X1 function. For example, an expression construct comprising a CaMK-X1 gene may be introduced into a cell line under conditions that allow expression. The level of CaMK-X1 activity is determined by a functional assay, for example detection of protein phosphorylation. Alternatively, candidate agents are added to a cell that lacks functional CaMK-X1, and screened for the ability to reproduce CaMK-X1 in a functional assay.

The compounds having the desired pharmacological activity may be administered in a physiologically acceptable carrier to a host for treatment of cancer, etc. The compounds may also be used to enhance CaMK-X1 function in wound healing, cell growth, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–10 wt %.

Formulations

The compounds of this invention can be incorporated into a variety of formulations for therapeutic administration. Particularly, agents that modulate CaMK-X1 activity, or CaMK-X1 polypeptides and analogs thereof are formulated for administration to patients for the treatment of CaMK-X1 dysfunction, where the CaMK-X1 activity is undesirably high or low, e.g. to reduce the level of CaMK-X1 in cancer cells. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intra-tracheal, etc., administration. The CaMK-X1 may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of disease, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 $\mu$g to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

For preparing the liposomes, the procedure described by Kato et al. (1991) *J. Biol. Chem.* 266:3361 may be used.

Briefly, the lipids and lumen composition containing the nucleic acids are combined in an appropriate aqueous medium, conveniently a saline medium where the total solids will be in the range of about 1–10 weight percent. After intense agitation for short periods of time, from about 5–60 sec., the tube is placed in a warm water bath, from about 25–40° C. and this cycle repeated from about 5–10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Discovery of CaMK-X1 EST Sequence

The Genbank database was searched for ESTs showing similarity to known kinase domain-related proteins using the "basic local alignment search tool" program, TBLASTN, with default settings. Human ESTs identified as having similarity to these known kinase domain (defined as p<0.0001) were used in a BLASTN and BLASTX screen of the GenBank non-redundant (NR) database, searched against the sequence of the catalytic domain of CaMK-1 (Genbank hs2721–161).

ESTs that had top human hits with >95% identity over 100 amino acids were discarded. This was based upon the inventors' experience that these sequences were usually identical to the starting probe sequences, with the differences due to sequence error. The remaining BLASTN and BLASTX outputs for each EST were examined manually, i.e., ESTs were removed from the analysis if the inventors determined that the variation from the known kinase domain-related probe sequence was a result of poor database sequence. Poor database sequence was usually identified as a number of 'N' nucleotides in the database sequence for a BLASTN search and as a base deletion or insertion in the database sequence, resulting in a peptide frameshift, for a BLASTX output. ESTs for which the highest scoring match was to non-kinase domain-related sequences were also discarded at this stage.

Using widely known algorithms, e.g. "Smith/Waterman", "Fasta", "FastP", "Needleman/Wunsch", "Blast", "PSIBlast," homology of the subject nucleic acid to other known nucleic acids was determined. A "Local FastP Search" algorithm was performed in order to determine the homology of the subject nucleic acid invention to known sequences. Then, a ktup value, typically ranging from 1 to 3 and a segment length value, typically ranging from 20 to 200, were selected as parameters. Next, an array of position for the probe sequence was constructed in which the cells of the array contain a list of positions of that substring of length ktup. For each subsequence in the position array, the target sequence was matched and augmented the score array cell corresponding to the diagonal defined by the target position and the probe subsequence position. A list was then generated and sorted by score and report. The criterion for perfect matches and for mismatches was based on the statistics properties of that algorithm and that database, typically the values were: 98% or more match over 200 nucleotides would constitute a match; and any mismatch in 20 nucleotides would constitute a mismatch.

Analysis of the BLASTN and BLASTX outputs identified an EST sequence from IMAGE clone AA838372 that had potential for being associated with a sequence encoding a kinase domain-related protein, e.g., the sequence had homology, but not identity, to known kinase domain-related proteins. Further, CaMK-X1 was found to have sequence similarity to members of the calmodulin dependent protein kinase family. The reported nucleotide sequence of the 5' EST of the AA838372 IMAGE clone corresponds approximately to 400 nucleotides of SEQ ID NO:1. A search of the UniGene database revealed that the 5' EST of the AA838372 IMAGE clone represented a novel human gene.

After identification of CaMK-X1 ESTs were discovered, the clones were added to Kinetek's clone bank for analysis of gene expression in tumor samples. Gene expression work involved construction of unigene clusters, which are represented by entries in the "pks" database. A list of accession numbers for members of the clusters were assigned. Subtraction of the clusters already present in the clone bank from the clusters recently added left a list of clusters that had not been previously represented in Kinetek's clone bank. For each of the clusters, a random selection of an EST IMAGE accession numbers were chosen to keep the clusters. For each of the clusters which did not have an EST IMAGE clone, generation of a report so that clone ordering or construction could be implemented was performed on a case by case basis. A list of accession numbers which were not in clusters was constructed and a report was generateds.

The AA838372 IMAGE clone was sequenced using standard ABI dye-primer and dye-terminator chemistry on a 377 automatic DNA sequencer. Sequencing revealed that the sequence corresponds to nucleotides 1 to 2447 of SEQ ID NO:1. Analysis of this gene fragment revealed that the gene product is a novel kinase domain-related protein, thereafter termed CaMK-X1.

Example 2

Rapid Amplification of cDNA Ends (RACE)

The gene specific oligodeoxynucleotide primer 5'-GGAGGGCG AGGAAACTGGGGAAG-3' (SEQ ID NO:3) was designed and then used to construct full length CaMK-X1 cDNA by 5 prime RACE (rapid amplification of cDNA ends; Frohman et al. 1988, *Proc. Natl. Acad. Sci. USA* 85:8898–9002). Adaptor primer (AP1) was used as sense primer, and SEQ ID NO:3 was used as antisense primer. A nested primer strategy was used on fetal brain cDNA provided with a Marathon-Ready™ RACE kit (Clontech, Palo Alto, Calif.). Following this, thermal cycling on a PE DNA Thermal Cycler 480 was done. When cycling was completed, the PCR product was analyzed, along with appropriate DNA size markers, on a 1.0% agarose/EtBr gel.

The product so obtained comprised a CaMK-X1 polynucleotide having the sequence of SEQ ID NO:1. BLASTX analysis indicated that the starting methionine residue was present at nucleotide 10, and that an upstream in-frame stop codon was present at nucleotide 1498, and the longest ORF (SEQ ID NO:1) predicted a protein of 476 amino acids (SEQ ID NO:2).

Example 3

Expression Analysis

The expression of CaMK-X1 was determined by Northern Blot, and dot blot analysis, and the protein was found to be upregulated in several tumor samples. In normal tissue, CaMK-X1 is highly expressed in brain, and at lower levels in kidney and spleen.

Dot Blot Preparation. Total RNA was purified from clinical cancer and control samples taken from the same patient. Samples were used from both liver and colon cancer samples. Using reverse transcriptase, cDNAs were synthesized from these RNAs. Radiolabeled cDNA was synthesized using Strip-EZ™ kit (Ambion, Austin, Tex.) according to the manufacturer's instructions. These labeled, amplified cDNAs were then used as a probe, to hybridize to human protein kinase arrays comprising human CaMK-X1. The amount of radiolabeled probe hybridized to each arrayed EST clone was detected using phosphorimaging.

The expression of CaMK-X1 was substantially upregulated in the tumor tissues that were tested. The data is shown in Table 1, expressed at the fold increase over the control non-tumor sample.

nucleotides in length. The mRNA was expressed at low levels in the kidney and spleen. The mRNA in the Northern blot ran at a position consistent with a molecular weight between 2.5–2.7 kb.

Rapid Amplification of cDNA Ends (RACE).

The gene specific oligodeoxynucleotide primer 5'-GGAGGGCG AGGAAACTGGGGAAG-3' (SEQ ID NO:4) was designed and then used to construct full length CaMK-X1 cDNA by 5 prime RACE (rapid amplification of cDNA ends; Frohman et al. 1988, *Proc. Natl. Acad. Sci. USA* 85:8898–9002). Adaptor primer (AP1) was used as sense primer, and SEQ ID NO:3 was used as antisense primer. A nested primer strategy was used on fetal brain cDNA provided with a Marathon-Ready™ RACE kit (Clontech, Palo Alto, Calif.). Following this, thermal cycling on a PE DNA Thermal Cycler 480 was done. When cycling was completed, the PCR product was analyzed, along with appropriate DNA size markers, on a 1.0% agarose/EtBr gel.

The product so obtained comprised a CaMK-X1 polynucleotide having the sequence of SEQ ID NO:1. BLASTX analysis indicated that the starting methionine residue was present at nucleotide 10, and that an upstream in-frame stop codon was present at nucleotide 1498, and the longest ORF (SEQ ID NO:1) predicted a protein of 476 amino acids (SEQ ID NO:2).

Homology analysis of the deduced amino acid sequence of CaMK-X1 revealed strong sequence identity with CaMK I from amino acid residues 11 to 333. The corresponding region of CaMK I contains the threonine residue required for activation and the regulatory domain that folds over the active site unless bound by CaM (Matsuchita et al. (1998) *Journal of Biological Chemistry* 273, 21473–21481). CaMK-X1 also has a region between residues 23 and 277 that is highly homologous (46% identity) to the highly conserved serine/threonine kinase active site.

Expression Analysis

The expression of CaMK-X1 was determined by Northern Blot, and dot blot analysis, and the protein was found to be upregulated in several tumor samples. In normal tissue, CaMK-X1 is highly expressed in brain, and at lower levels in kidney and spleen.

Dot Blot Preparation. Total RNA was purified from clinical cancer and control samples taken from the same patient. Samples were used from both liver and colon cancer samples. Using reverse transcriptase, cDNAs were synthesized from these RNAs. Radiolabeled cDNA was synthesized using Strip-EZ™ kit (Ambion, Austin, Tex.) according

TABLE 1

|  | liver 1 | liver 2 | liver 3 | colon 1 | colon 2 | colon 3 | colon 4 | colon 5 | colon 6 | colon 7 |
|---|---|---|---|---|---|---|---|---|---|---|
| CaMK-X1 | 5.0 | 4.9 | 5.1 | 2.3 | 2.6 | 1.5 | 3.3 | 1.2 | 1.3 | 4.05 |

Northern Blot Analysis: CaMK-X1 was used to probe and blot mRNA, using a commercially available poly-A+ selected blot (Clontech, Palo Alto, Calif.), and hybridized according to the manufacturer's instructions. The CaMK-X1 clone (corresponding to SEQ ID NO:1) was radiolabeled using Strip-EZ PCR kit (Ambion, Austin, Tex.) according to the manufacturer's instructions.

The results are shown in FIG. 1. It can be seen that in normal tissues, CaMK-X1 is expressed at high levels in the brain, hybridizing to an mRNA of approximately 2,700 to the manufacturer's instructions. These labeled, amplified cDNAs were then used as a probe, to hybridize to human protein kinase arrays comprising human CaMK-X1. The amount of radiolabeled probe hybridized to each arrayed EST clone was detected using phosphorimaging.

The expression of CaMK-X1 was substantially upregulated in the tumor tissues that were tested. The data is shown in Table 3, expressed at the fold increase over the control non-tumor sample.

TABLE 3

| | liver 1 | liver 2 | liver 3 | colon 1 | colon 2 | colon 3 | colon 4 | colon 5 | colon 6 | colon 7 |
|---|---|---|---|---|---|---|---|---|---|---|
| CaMK-X1 | 5.0 | 4.9 | 5.1 | 2.3 | 2.6 | 1.5 | 3.3 | 1.2 | 1.3 | 4.05 |

Functional Assays

A deletion mutant clone was created to aid in the characterization of this kinase in vivo. In addition, it is shown that CaMK-X1 phosphorylates CREB at Ser 133 in Jurkat cells, and this phosphorylation is controlled by a Calmodulin binding site.

CaMK-X1 kinase activity was shown in vitro using three different approaches. CaMK-X1 was purified from Hi5 insect cells and HEK293 cells overexpressing CaMK-X1 using GST and Ni2+ affinity chromatography. Furthermore, CaMK-X1 was purified via immunoprecipitation using a monoclonal antibody directed against the X-press fusion protein. CaMK-X1 displays no activity toward exogenous substrates in the absence of Ca2+ and calmodulin. In the presence of Ca2+ and calmodulin, CaMK-X1 phosphorylated Syntide and CREBtide peptides. This is the first experimental demonstration that CaMK-X1 behaves as a calcium/calmodulin-dependent protein kinase.

Cloning and Sub-cloning. Cloning of CaMK-X1 and construction of cDNA expression vectors and the CaMK-X1 deletion mutant: A human brain cDNA library was used with a 5' RACE system. To generate the full-length cDNA of CaMK-X1, a pair of primers were designed and used in the PCR reaction. (SEQ ID NO:5) 5'-GTGGAGGGC GAGGAAACTGGGGMG-3 and (SEQ ID NO:6) 5'-CTCGAGTCACA TAATGAGACAGACTCCAGTC. The coding area of CaMK-X1 was amplified using the above pair of primers. The amplification product was then cloned into a Promega T/A vector and subsequently cloned into other vectors as necessary. The EcoRI and XhoI fragment of CaMK-X1 was cloned into bacterial expression vector pGEX-4T-3 and mammalian expression vector pcDNA3.1/ His B. All constructs were verified by restriction enzyme digestion and DNA sequencing.

Tissue Distribution of CaMK-X1. CaMK-X1 was used to probe and blot mRNA, using a commercially available poly-A+ selected blot (Clontech, Palo Alto, Calif.), and hybridized according to the manufacturer's instructions. The CaMK-X1 clone (corresponding to SEQ ID NO:1) was radiolabeled using Strip-EZ PCR kit (Ambion, Austin, Tex.) according to the manufacturer's instructions.

It was found that in normal tissues, CaMK-X1 is expressed at high levels only in the brain, hybridizing to an mRNA of approximately 2.8 Kb in length. The mRNA was expressed at low levels in the kidney and spleen. The mRNA in the Northern blot ran at a position consistent with a molecular weight between 2.5–2.7 kb.

CaMK-X1 increases proliferation of Cos 7 cells. The proliferation rate of Cos 7 cells when transfected with CaMK-X1 was examined. To determine whether increased levels of CaMK-X1 had any effect on cell proliferation, Cos 7 cells were transfected with increasing concentrations of CaMK-X1 or vector plasmids in the presence of KCl. Cell proliferation was measured by standard protocols. As shown in FIG. 1, transfection of CaMK-X1 increased the rate of proliferation, whereas the same concentration of vector alone decreased the rate of proliferation. The proliferation rate of Cos 7 cells transiently transfected with CaMK-X1 is higher in 5% serum that at the 2.5% or 0.5%, suggesting that CaMK-X1 induced proliferation is modulated by serum. This data demonstrates that CaMK-X1 can promote cell proliferation.

CaMK-X1 Phosphorylates CREB in vivo. cAMP response element-binding protein (CREB) is a DNA binding transcription factor. A number of growth factors and hormones have been shown to stimulate the expression of cellular genes by inducing the phosphorylation of the nuclear factor CREB at Ser 133 (Montminy (1997) Annu.Rev. Biochem. 66:807–822). Originally characterized as a target for PKA-mediated phosphorylation, CREB is also recognized by other kinases including Protein kinase C, calmodulin kinase, microtubule-activated protein kinase activated protein, and protein kinase B/AKT.

It was investigated whether CaMK-X1 could regulate CREB-Ser 133 phophorylation in vivo. To analyze CaMK-X1 in vivo, Jurkat cells were utilised. Jurkat cells transfected with various concentrations of plasmids carrying CaMK-X1 or vector were stimulated with KCl. Whole cell protein was prepared from these transfected cells and the phosphorylation status of CREB at Ser 133 was determined. Detection of CREB phosphorylation was carried out using anti-phospho-CREB antibody. Phosphorylation of CREB increased with increasing amounts of the CaMK-X1 gene transfection, but only in the presence of $Ca^{2+}$.

To assess the effects of intracellular $Ca^{2+}$ on CaMK-X1, transfected Jurkat cells were treated with 30 mM KCl. KCl depolarizes cell membranes thereby creating an increase in intracellular $Ca^{2+}$. Addition of KCl resulted in significant phosphorylation of CREB only in cells transfected with CaMK-X1. These results show that CaMK-X1 is activated by $Ca^{2+}$ and subsequently phosphorylates CREB at Ser 133 in Jurkat cells.

Calmodulin binding site deletion mutant of CaMK-X1 constitutively phosphorylates CREB in vivo. It has been shown previously that CaM kinases can be made $Ca^{2+}$ independent by truncation of the calmodulin binding site. Similarly, a constitutively active form of CaMK-X1 was created by removing the putative CaM-binding domain via truncation at amino acid Gln 301. This deletion site eliminates the two predicted $Ca^{2+}$/Calmodulin-binding sites in the autoinhibitory domain. The truncated gene was placed in a pcDNA mammalian expression vector for transfection experiments.

To analyze the function of the mutant CaMK-X1 in vivo, Jurkat cells were used. Jurkat cells transfected with various concentrations of plasmids carrying CaMK-X1 or vector were stimulated with KCl. Whole cell protein was prepared from these transfected cells and the phosphorylation status of CREB at Ser 133 was determined. Detection of CREB phosphorylation was carried out using anti-phospho-CREB antibody. Mock treatment by the vectors did not have any effect on CREB phosphorylation. The transfection of wild type CaMK-X1 had no effect on CREB phosphorylation; however, addition of KCl to wild type transfected Jurkat cellsresulted in significant CREB phosphorylation. Transfection of the deletion mutant had a significant effect on CREB phosphorylation without the addition of KCl. These results demonstrate that truncation of wild type CaMK-X1 at Gln 301 converted the enzyme to a $Ca^{2+}$/CaM-independent state.

Expression of CaMK-X1 kinase in HEK293 cells. The availability of the CaMK-X1 clone allows us to reconstruct the signaling pathway. This allows us to identify downstream components such as transcription factors or modification -of protein components such as phosphorylation, proteolytic processing, methylation, and the like, which finds use in drug screening.

To characterize CaMK-X1 at the protein level, HEK293 cells were transfected with pcDNA3-Xpress (Invitrogen) containing the CaMK-X1 coding sequence fused to the Xpress epitope; and stable cell lines were created using standard techniques. Five stable cell lines containing the pcDNA-CaMK-X1 plasmid and five containing the vector only control were selected and CaMK-X1 expression levels were determined. Whole cell extracts were prepared from each cell line. The cell lysates were analysed by Western blotting with an anti Xpress monoclonal antibody. These experiments revealed a 53 kDa fusion protein present in the CaMK-X1 transfected cells that was absent in the control cells.

The transfected HEK293 cells stably expressed CaMK-X1 as an Xpress fusion protein. Similarly, we have detected a GST-CaMK-X1 fusion protein expressed in Hi5 cells. Glutathione-sepharose affinity chromatography was used to purify the GST-CaMK-X1 fusion protein. Glutathione-sepharose purified CaMK-X1 and anti-Xpress antibody immunoprecipitated CaMK-X1 were subjected to Western blot analysis. This Western blot indicates that CaMK-X1 can be purified from both transfected HEK293 cell lysate and Hi5 cell lysate. These methodologies were used to purify CaMK-X1 for further characterization.

A protein with a molecular mass of 53 kDa was identified when lysates of HEK293 cells transfected with the Xpress-CaMK-X1 clone were subjected to immunoprecipitation with anti-Xpress antibody followed by anti-X-press Western blotting, which band was absent with vector alone transfected cells. This data confirms that the anti-X-press antibody selectively immunoprecipitated the fusion protein (X-press-CaMK-X1).

Figure 2:
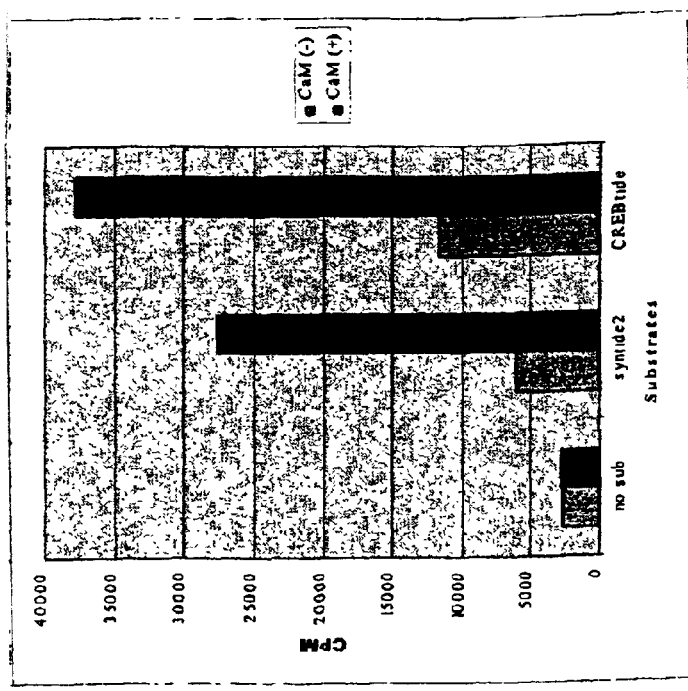
FIG. 2 is a graph depicting phosphorylation of CREBtide and Syntide 2 in vitro by CamKX1.
Figure 2:
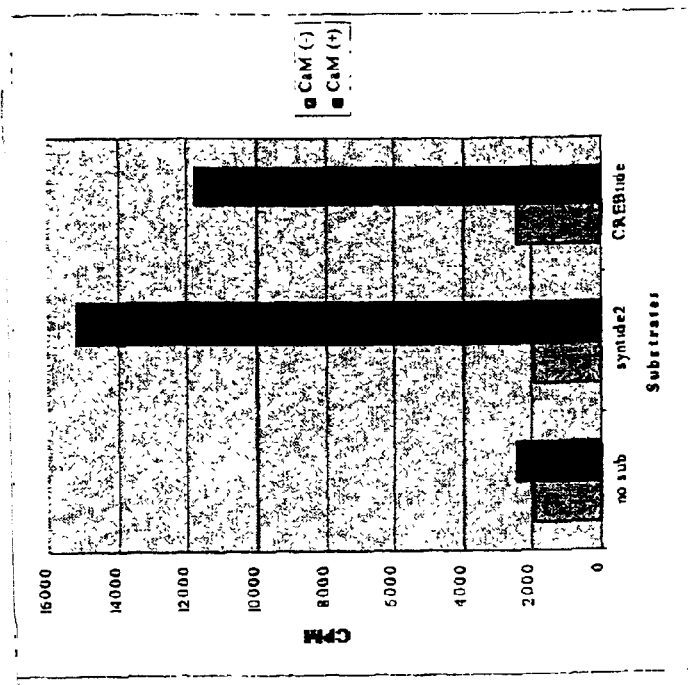

These immunoprecipitated materials were assayed for kinase activity, using the peptides (SEQ ID NO:7) CREBtide: Lys Arg Arg Glu Ile Leu Ser Arg Arg Pro Ser Tyr Arg; (SEQ ID NO:8) Syntide 2: Pro Leu Ala Arg Thr Leu Ser Val Ala Gly Leu Pro Gly Lys Lys; and (SEQ ID NO:9) Calmodulin Dependent Protein Kinase Substrate: Pro Leu Ser Arg Thr Leu Ser Val Ser Ser. The immunoprecipitated materials were subjected to an in vitro kinase assay as described above. Since it was shown that CaMK-X1 phosphorylates CREB in vivo, it was reasoned that CaMK-X1 would phosphorylate CREBtide and Syntide 2 (Colbran et al. (1989) *J Biol Chem* 264(9):4800–4804). As predicted, CaMK-X1 phosphorylated CREBtide and Syntide 2 in vitro. In contrast, CaMK-X1 could not phosphorylate control peptide. The degree of phosphorylation is augmented in the presence of calmodulin, as shown in FIG. 2. In the absence of a substrate, there is no significant incorporation of radioactive material ($^{32}P$) indicating that CaMK-X1 does not autophosphorylate under these assay conditions. This demonstrates that immunoprecipitated CaMK-X1 possesses a kinase activity and that this kinase activity is capable of phosphorylating peptides in vitro. These studies also revealed that CaMK-X1 requires calmodulin for efficient activity.

Catalytic activity and comparison of substrate specificities of CaMK-X1. In order to determine if CaMK-X1 is an active kinase in vitro, the clone was Histidine tagged, expressed in Sf9 cells and purified with a Ni2+ affinity column. For analysis of substrate specificity, we tested the following three peptides; CREBtide, Syntide 2 and CDPK-peptide (control peptide). In vitro kinase assays were then performed. As described above, CREBtide and Syntide 2 are phosphorylated by the purified CaMK-X1. The rate of phosphorylation is increased in the presence of $Ca^{2+}$ and calmodulin. Compared to a no substrate control, addition of the peptides resulted in significant $^{32}P$ incorporation. These results indicate that CaMK-X1 phosphorylates these peptides in vitro. Our studies also revealed Syntide 2 and CREBtide had higher incorporation of $^{32}P$ than the control peptide. These observations further confirm the in vivo data. Summary. We have demonstrated that CaMK-X1 phosphorylates CREB in cells and in vitro at Ser 133. We have also demonstrated CaMK-X1 kinase activity in vitro. We were able to purify CaMK-X1 from transfected Hi5 insect cells and from a HEK293 cell line overexpressing CaMK-X1 using glutathione-sepharose and Ni2+ affinity chromatography. Furthermore, CaMK-X1 was purified by immunoprecipitation using a monoclonal antibody directed against the Xpress fusion protein. CaMK-X1 displays no activity toward exogenous substrates in the absence of $Ca^{2+}$ and calmodulin. In the presence of $Ca^{2+}$ and calmodulin, CaMK-X1 phosphorylated Syntide 2 and CREBtide. These results indicate that Camk X-1 are involved in human pathology.

Materials.

Dulbecco's Modified Eagle Medium (DMEM), RPMI Medium 1640, L-glutamine, phosphate buffered solution (PBS), fetal bovine serum (FBS), and restriction enzymes were from GibcoBRL. TOPO cloning kit (including PCR materials and pCR 2.1-Topo vector) were from Invitrogen. Phospho-CREB (Ser133) polyclonal rabbit antibody was from Cell Signaling Technology. 96- and 6-well delta surface plates were from NUNCLON. QIAprep Spin Miniprep Kit was from Qiagen. Wizard Plus Minipreps DNA Purification System (for gel extractions) (Promega). FuGENE 6 Transfection Reagent was from Boehringer Mannheim. pcDNA3.1 mammalian expression vector (Invitrogen). Western Blotting Luminol Reagent was from Santa Cruz Biotechnology. 2° goat-anti-rabbit IgG (H+L) HRP conjugated antibody was from Bio-Rad Laboratories.

Cloning of Full Length CaMK-X1. To generate the full-length cDNA of CaMK-X1, a pair of primers were designed and used in the PCR reaction. (SEQ ID NO:10) 5'-GAATTCAATGGGTCGAAAGGAAGAAGATGA and (SEQ ID NO:11) 5'-CTCGAGTCACATAATGAGACAGACTCCAGTC. The amplification product was cloned into cloning vectors through restriction sites EcoRI and XhoI. The EcoRI and XhoI fragment was cloned into bacteria expression vector pGEX-4T-3 and mammalian expression vector pcDNA3.1/HisB. All constructs were verified by restriction enzyme digestion and DNA sequencing.

Construction of Deletion Mutant CaMK-X1CA. A deletion mutant was created using these oligonucleotides EcoRI (SEQ ID NO:12) 5'-GAATTCAATGGGTCGAAAGGAAGAAGATGA-3' forward, and XhoI (SEQ ID NO:13) 5'-CTCGAGCTGGATCTGGAGGCTGACTGATGG-3' reverse. The resulting PCR fragment was cloned into mammalian expression vector pcDNA 3.1.

Cell Culture. Cells were incubated at 37° C. in 5% $CO_2$ (standard conditions). All cells, unless mentioned below, were cultured in DMEM with FBS; the specific amount of FBS varies and is stated in the report for each result. Jurkat cells were cultured in RPMI Medium 1640 with added glucose, L-glutamine, and 10% FBS.

Cell Transfection. Cells were seeded to a density of $2\times10^5$ in 6 well plates (in appropriate media for the particular cell line) and incubated for 24 hours under standard conditions. 3 ml of FuGENE 6 transfection reagent was diluted in 97 ml of serum-free media (appropriate for the cell line being transfected) and left for 5 minutes at room temperature; that was then added drop-wise to the desired amount of plasmid DNA (in pcDNA3.1) and left for 10 minutes at room temperature. The finished transfection solution was then added drop-wise to the cells, which were then incubated for 24 hours under standard conditions.

Proliferation Assay. The media from 6 well plates was removed and trypsin was added to digest the extracellular matrix holding the cells to the plate; media (appropriate to the cell type) was then added to deactivate the trypsin. The cells and media were transferred into Falcon tubes, centrifuged, and the supernatant was discarded. The cells were resuspended in appropriate media. 3000 cells were seeded in each well of a 96 well plate and appropriate media was added up to 90 ml. Ten $\mu$l of 0.1 Ci/L $^3$H-thymidine was added to each well. The plates were then incubated for 24 hours under standard conditions. Twenty-five $\mu$l of cold trichloroacetic acid was added to each well and the plates were kept at $4°$ C. for 2 hours. The plates were then washed in cold running water and allowed to dry. Proliferation was determined by incorporation of thymidine as measured via scintillation counting.

Cell lysis. Lysis buffer was 50 mM Hepes (pH 7.5), 150 mM NaCl, 1% NP-40, 2 mM NaF, 1 mM $Na_3VO_4$, 1 mM PMSF, 1 mg/ml pepstatin, 1 mg/ml leupeptin, 1 mg/ml aprotinin, and 20 mM $\beta$-glycerophosphate. For adherent cells, the media was removed from the 6 well plate, the wells were washed with PBS which was then removed, the plates were put on ice and 40 ml of lysis buffer was then added to each well. Crude lysates were collected with a cell scraper and placed in an Eppendorf tube. For non-adherent cells, the media and cells were transferred from a 6-well plate to tubes, centrifuged and the supernatant removed; 40 ml of lysis buffer was then added. All crude lysates were then vortexed and left on ice for 10 minutes. The crude lysates were centrifuged at 14,000 RPM for 10 minutes at $4°$ C. and the supernatant, the final lysate, was transferred to new tubes.

Western Blotting. Equal weights of cell lysate proteins were mixed with 4x loading buffer, boiled for five minutes and were then briefly centrifuged. The samples were run on a 10% SDS-PAGE and were then transferred to PVDF membranes which were washed with TTBS and blocked with 2% BSA. They were blotted with primary antibody for 16 hours at $4°$ C. The membranes were washed with TTBS, blotted with secondary antibody for 1 hour and washed with TTBS. The luminol reagent was added, the blot was placed on film and the autoradiograph developed.

Expression and Purification of CaMK-X1 Protein. The human CaMK-X1 gene (K283) was sub-cloned into baculovirus transfer vector pAcG4T3 derived from pAcG2T (BD Biosciences) under the control of the strong AcNPV (Autograpga californica Nuclear Polyhedrosis Virus) polyhedrin promoter. This was co-transfected with linear BaculoGold DNA in Spodoptera frugiperda Sf9 cells following standard procedure (BD Biosciences). The GST-CaMK-X1 recombinant baculovirus was amplified in Sf9 cells in TNM-FH medium (JHR Biosciences) with 10% fetal bovine serum. The GST-CaMK-X1 protein was expressed in approximately $5\times10^8$ Hi-5 cells (Invitrogen) in 500 ml of Excell-400 medium (JHR Biosciences) at a multiplicity of infection (MOI) of five for a period of 72 h in a spinner flask. The cells were harvested at 800x g for 5 min at $4°$ C. The pellet was lysed in 40 ml of Lysis Buffer (50 mM Tris-HCl, PH7.5, 2.5 mM EDTA, 150 mM NaCl, 1% NP-40, 0.1% $\beta$-mercaptoethanol, 10 $\mu$g/ml DNase I, 0.5 mM sodium orthovanadate, 50 mM $\beta$-glycerophosphate, 0.1 mM PMSF, 1 mM benzamidine, 2 $\mu$g/ml aprotinin, 2 $\mu$g/ml leupeptin, 1 $\mu$g/ml pepstatin) by sonication and centrifuged at 10,000x g at $4°$ C. for 15 min. The supernatant was loaded on a column containing 2.5 ml of glutathione-sepharose (Sigma). The column was washed with Wash Buffer A (50 mM Tris-HCl, pH 7.5, 1 mM EDTA, 500 mM NaCl, 0.1% $\beta$-mercaptoethanol, 0.1% NP-40, 0.1 mM sodium orthovanadate, 50 mM $\beta$-glycerophosphate, 0.1 mM PMSF, 1 mM benzamidine) until OD280 returned to baseline, then Wash Buffer B (50 mM Tris-HCl, PH7.5, 1 mM EDTA, 50 mM NaCl, 0.1% $\beta$-mercaptoethanol, 0.1 mM PMSF). The GST-CaMK-X1 protein was eluted in Elution Buffer (50 mM Tris-HCl, PH7.5, 1 mM EDTA, 50 mM NaCl, 0.1% $\beta$-mercaptoethanol, 10 mM glutathione, 10% glycerol). The fraction was aliquoted and stored at $-70°$ C.

CaMK-X1 in vitro assay. CaMK-X1 was assayed at room temperature for 15 min in 50 mM HEPES, pH 8.0, 10 mM $MgCl_2$, 1 mM dithiothreitol, 0.005% Tween 20, 1 mM $CaCl_2$, 1.5 mM calmodulin (CalBiochem), 50 uM $[\gamma-^{32}P]$-ATP and 0.2 $\mu$g/$\mu$l Syntide 2 (American Peptide Company) or CREBtide (CalBiochem) in a final volume of 25 $\mu$l. Reactions were initiated by addition of $[\gamma-^{32}P]$-ATP and terminated by spotting 10 $\mu$l of the reaction mixture onto P81 paper followed by washing in 1% phosphoric acid.

Immunoprecipitation. For immunoprecipitations, HEK293 cells in 35 mm dishes stably expressing CaMK-X1-X-press plasmid were washed twice in ice-cold PBS and lysed in solution containing 50 mM Tris/HCl, pH 7.6, 2 mM EGTA, 2 mM EDTA, 2 mM dithiothreitol, protease inhibitors aprotinin (10 $\mu$g/ml) leupeptin (100 $\mu$g/ml) pepstatin (0.7 $\mu$g/ml), 1 mM 4-(2-aminoethyl) benzenesulfony fluoride hydrochloride, and 1% Triton X-100 (Lysis buffer). Proteins were immunoprecipitated with the anti-X-press antiserum (1:100 dilution) or with control serum. The immuno complexes were recovered using protein G Sepharose.

In vitro kinase assay with immunoprecipitated materials. CaMK -X1 was eluted from the immunocomplexes as described in the previous section and 20 $\mu$l of the eluate was mixed with 20 $\mu$l of phosphorylation mix containing 100 $\mu$M $[\gamma\ ^{32}P]$ ATP (specific activity, 400–600 cpm/pmol), 30 mM Tris, pH 7.4, 30 mM $MgCl_2$, 1 mM DTT, and 250 nM peptide and incubated for 10–15 minutes at $30°$ C.

Northern Blot Analysis. Northern blot analysis was performed using an $[\alpha\ ^{32}P]$ dCTP-labeled CaMK-X1 cDNA fragment corresponding to bases 1.2 kb of human CaMK-X1 according to standard procedures (Ambion). RNA from several primary human tissues was analyzed with commercially available poly(A)+RNA blots (CLONTECH) The blotted membrane was dried and autoradiographed.

CaMK-X1 Activity Assay. Equivalent concentrations of purified CaMK-X1 preparations were incubated using a Beckman Biomek 2000 robotic system. Each well (96 well microtiter plate) contained 15 $\mu$l reaction mixture composed of 50 mM HEPES, pH 8.0, 10 mM $MgCl_2$, 1 mM dithiothreitol, 0.005% Tween 20, 1 mM $CaCl_2$, 1.5 mM Calmodulin (CalBiochem) 50 $\mu$M $\gamma-^{32}P$ ATP (200 cpm/pmol) and 0.2 $\mu$g/$\mu$l Syntide 2 (American Peptide Company) or CREBtide (CalBiochem) in a final volume of 25 $\mu$l. The reaction was initiated by addition of $[\gamma^{32}-P]$-ATP and terminated by spotting 10 $\mu$l of the reaction mixture into a 96 well Millipore Multiscreen plate. The Multiscreen plate was washed in 1% phosphoric acid, dried and counted in a Wallac Microbeta scintillation counter.

What is claimed is:

1. An isolated nucleic acid molecule, wherein said nucleic acid comprises the nucleotide sequence of SEQ ID NO:1.

2. A vector comprising the nucleic acid molecule claim 1.

3. The vector of claim 2, wherein said vector comprises a transcription cassette operably linked to said isolated nucleic acid molecule.

4. The vector of claim 3, wherein said vector is a plasmid.

5. The vector of claim 3, where said vector is a retrovirus.

6. The vector of claim 3, wherein said vector is an adenovirus.

* * * * *

UNITED STATES PATENT AND TRADEMARK OFFICE
CERTIFICATE OF CORRECTION

PATENT NO. : 6,830,925 B2  Page 1 of 1
APPLICATION NO. : 09/960643
DATED : December 14, 2004
INVENTOR(S) : Yoganathan et al.

It is certified that error appears in the above-identified patent and that said Letters Patent is hereby corrected as shown below:

On the title page (73), add the following Assignee: --University of British Columbia, Vancouver (CA)--

Signed and Sealed this

Thirty-first Day of October, 2006

JON W. DUDAS
*Director of the United States Patent and Trademark Office*